(12) United States Patent
Sunazuka et al.

(10) Patent No.: US 9,248,067 B2
(45) Date of Patent: Feb. 2, 2016

(54) MEDICAL IMAGING APPARATUS AND BED FOR MEDICAL IMAGING APPARATUS

(71) Applicants: Izumi Sunazuka, Tokyo (JP); Satoshi Iizuka, Tokyo (JP)

(72) Inventors: Izumi Sunazuka, Tokyo (JP); Satoshi Iizuka, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 0 days.

(21) Appl. No.: 14/354,265

(22) PCT Filed: Nov. 14, 2012

(86) PCT No.: PCT/JP2012/079461
§ 371 (c)(1),
(2) Date: Apr. 25, 2014

(87) PCT Pub. No.: WO2013/073551
PCT Pub. Date: May 23, 2013

(65) Prior Publication Data
US 2014/0259411 A1    Sep. 18, 2014

(30) Foreign Application Priority Data
Nov. 18, 2011    (JP) ................................. 2011-252298

(51) Int. Cl.
| A61G 13/10 | (2006.01) |
| A61B 5/055 | (2006.01) |
| A61B 6/03  | (2006.01) |
| A61B 6/04  | (2006.01) |
| A61B 6/00  | (2006.01) |

(52) U.S. Cl.
CPC .............. *A61G 13/10* (2013.01); *A61B 5/0555* (2013.01); *A61B 6/035* (2013.01); *A61B 6/0407* (2013.01); *A61B 6/0457* (2013.01); *A61B 6/4405* (2013.01); *A61B 6/4411* (2013.01)

(58) Field of Classification Search
CPC ...................................................... A61G 13/10
USPC .............. 5/600–601; 378/195, 205, 208–209; 600/415
See application file for complete search history.

(56) References Cited

U.S. PATENT DOCUMENTS

| 6,776,527 B1 * | 8/2004 | Tybinkowski et al. ........ 378/209 |
| 2005/0020906 A1 | 1/2005 | Seijger et al. |
| 2005/0034237 A1 | 2/2005 | Lenting et al. |
| 2006/0167356 A1 | 7/2006 | Everett et al. |

FOREIGN PATENT DOCUMENTS

| JP | 2005-508691 | 4/2005 |
| JP | 2006-507868 | 3/2006 |

OTHER PUBLICATIONS

International Search Report in PCT/JP2012/079461.

\* cited by examiner

*Primary Examiner* — Fredrick Conley
(74) *Attorney, Agent, or Firm* — Cooper & Dunham LLP

(57) ABSTRACT

Provided is a narrow docking mechanism that enables a bed and an apparatus main body to be coupled together with sufficient holding force during docking and that does not hinder access by an examiner to an object. A coupling mechanism on a bed 3 side includes a coupling plate 7 having one end fixed to the bed 3, and a coupling mechanism 50 on the main apparatus side includes a plurality of rollers 12 arranged side by side along the shape of both sides of the coupling plate 7. As the plurality of rollers 12 sandwiches and holds the coupling plate 7 from both sides, the coupling plate 7 can attach to and detach from the bed 3 by coupling the bed to the apparatus main body so as to be inserted between the arranged rollers 12.

14 Claims, 15 Drawing Sheets

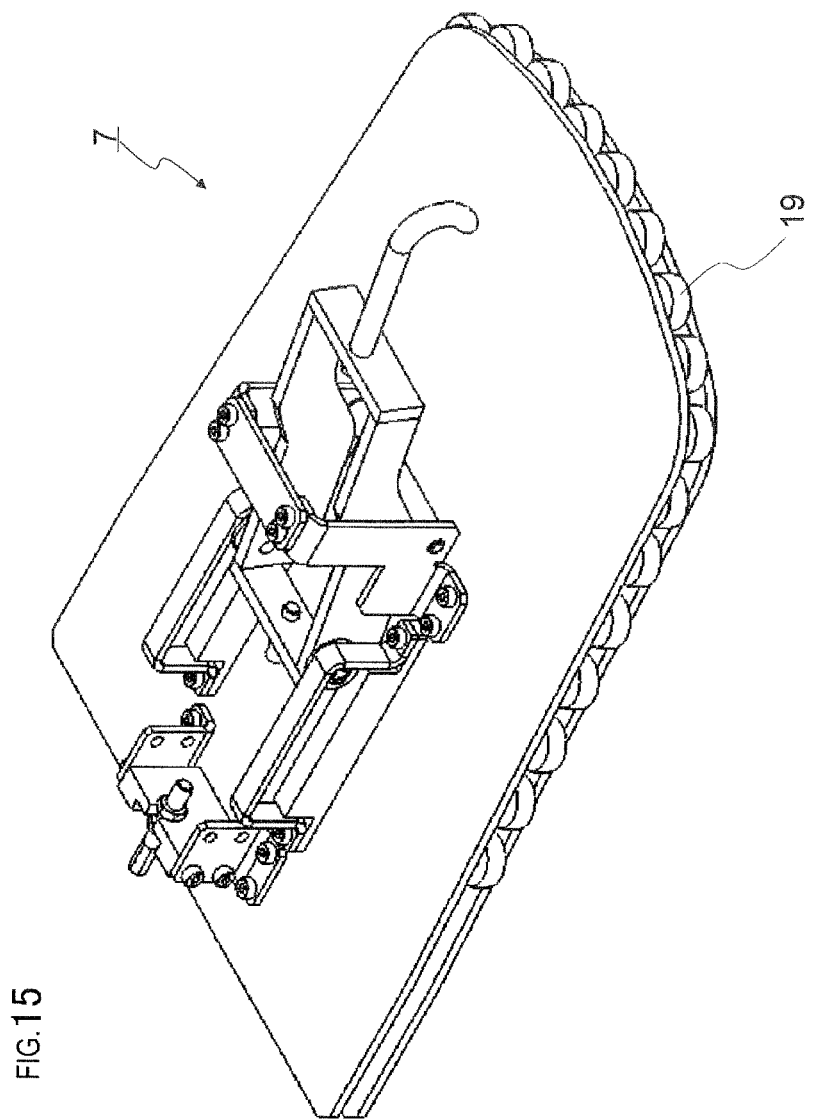

MEDICAL IMAGING APPARATUS AND BED FOR MEDICAL IMAGING APPARATUS

TECHNICAL FIELD

The present invention relates to a medical imaging apparatus, and particularly, to a bed that is attachable to and detachable from an apparatus main body.

BACKGROUND ART

Medical imaging apparatuses, such as a magnetic resonance imaging (hereinafter referred to as an MRI) apparatus and a CT apparatus, have a structure in which an object is mounted on a bed and the bed is inserted into an imaging space of an apparatus main body. Therefore, the bed has a complicated configuration including a lifting mechanism that lifts a top plate, on which the object is mounted, to the height of the imaging space of the apparatus main body, a horizontal movement mechanism that horizontally moves the top plate in order to insert an imaging site of the object up to the center of the imaging space, a control unit that performs the movement according to a control signal from the apparatus main body, or the like. For this reason, the bed usually has a weight of hundreds of kilograms, is precisely positioned, and is mechanically and electrically connected to the apparatus main body.

In recent years, for an improvement in the throughput of examination for objects, beds that are usable after being separated from the apparatus main body are required. For example, in the case of an object that cannot enter a bed by itself, the work of transporting the object, which is transported to the vicinity of the bed, lifting the object by two or more examiners, and mounting and fixing the object to the bed is required, and examiner's burden is great. Particularly in the case of an MRI apparatus, metallic mobile beds, such as a usual stretcher, are drawn close to the apparatus main body by a strong magnetic field generated from the apparatus main body. Therefore, the object cannot be transported to the side of a bed fixed to the MRI apparatus by the usual mobile beds. Therefore, in the related art, an object is transported in a procedure of transferring the object from the usual stretcher to a special stretcher made of a nonmagnetic substance in the lobby of an examination room, and transporting the object to the side of the bed of the MRI apparatus. In this case, a transfer from a bed to the usual stretcher, a transfer from the usual stretcher to the nonmagnetic stretcher, and a transfer from the non-magnetic stretcher to the bed of the MRI apparatus are required, and the number of transfer times is three.

Therefore, if the bed of the MRI apparatus can be separated from the main body and be pushed with the hands and moved to the lobby of the examination room or the bedside of an object, and the object can be directly transferred from the usual stretcher or bed to the bed of the MRI apparatus, the number of times of transfer can be reduced. Accordingly, not only can an improvement in the throughput of examination be realized, but also a burden on the object can be reduced.

A bed that is attachable to and detachable from a main body of an MRI apparatus is disclosed in PTL 1. In this technique, as shown in FIGS. 1 to 5 of PTL 1, a front lower portion of the apparatus main body is equipped with a docking mechanism 16, such as a guide 24 having a conical outer shape. Meanwhile, a lower portion of a front end of a bed is equipped with a coupling mechanism to be coupled to the docking mechanism 16. When the bed is coupled to the apparatus main body, the bed is brought close to the apparatus main body until a lateral plate 100 arranged at a front end portion of the bed bumps against docking points 32 and 34 on both sides of an upper portion of the conical guide 24 of the apparatus main body. The movement of the bed at this time is guided as a pair of pins 96 and 98 below the lateral plate 100 are inserted so as to run along the conical guide 24 of the apparatus main body. If the lateral plate 100 of the bed bumps against the docking point 32, the bed is fixed to the apparatus main body by coupling a latch hook 58 of a lower portion of the bed to a pin member 56 at the tip of the conical guide 24 of the apparatus main body.

CITATION LIST

Patent Literature

[PTL 1] Specification of U.S. Pat. No. 4,567,894

SUMMARY OF INVENTION

Technical Problem

If the force of holding the bed by the apparatus main body is insufficient and shaking occurs in the bed after the bed is coupled to the apparatus main body, a fear of insecurity may given to an object when the object is made to get on and off the bed. Hence, the attachable and detachable bed is required to be held by the apparatus main body with sufficient force without being shaken also in the horizontal direction (width direction) of the bed.

In the technique of PTL 1, the bed and the apparatus main body are coupled together. However, since the bed and the apparatus main body are coupled together only in one place, that is, at a tip of the latch hook 58, the bed is likely to be shaken in a direction in which the bed turns around the coupling site. In the structure of PTL 1, as the lateral plate 100 at the lower portion of the bed bumps against the pair of docking points 32 and 34 of the apparatus main body, the shaking when the bed turns around the tip of the latch hook 58 is prevented. However, if the spacing between the docking points 32 and 34 is narrow, the shaking cannot be effectively prevented. For this reason, it is necessary to increase the spacing between the docking points 32 and 34 and the width of the lateral plate 100, and it is necessary to arrange a wide docking mechanism 16 at the lower portion of the apparatus main body and to fix a wide lateral plate 100 at the lower portion of the bed.

However, if the wide lateral plate 100 is fixed to the front end portion of the bed, when the bed is moved, the bed hits the legs of an examiner that stands by the bed, or hinders movement of the bed or a transfer operation of the object. As a result, operativity is deteriorated. Additionally, even after the bed is coupled to the apparatus main body, the wide docking mechanism and the wide lateral plate 100 hits the examiner's legs and hinders access of the object. As a result, operativity is deteriorated.

An object of the invention is to provide a narrow docking mechanism that enables a bed and an apparatus main body to be coupled together with sufficient holding force during docking and that does not hinder access to an object by an examiner.

Solution to Problem

In order achieve the above object, according to the invention, there is provided a medical imaging apparatus including an apparatus main body equipped with an imaging function of an object, a movable bed, and coupling mechanisms arranged on an apparatus main body side and on a bed side, respectively, in order to detachably couple the bed to the apparatus main body. The coupling mechanism on the bed side includes a coupling plate having one end fixed to the bed. The coupling mechanism on the apparatus main body side includes a plurality of rollers that are arranged side by side along the shape of both sides of the coupling plate of the bed when the bed is coupled to the apparatus main body. The plurality of rollers sandwiches and holds the coupling plate from both sides.

Advantageous Effects of Invention

According to the invention, it is possible to provide a bed that can be held with sufficient force during docking and is also excellent inaccessibility to an object on the bed.

BRIEF DESCRIPTION OF DRAWINGS

FIG. 15 is a perspective view of the coupling plate 7 including rollers at an outer periphery of the third embodiment.

DESCRIPTION OF EMBODIMENTS

Figure 1:
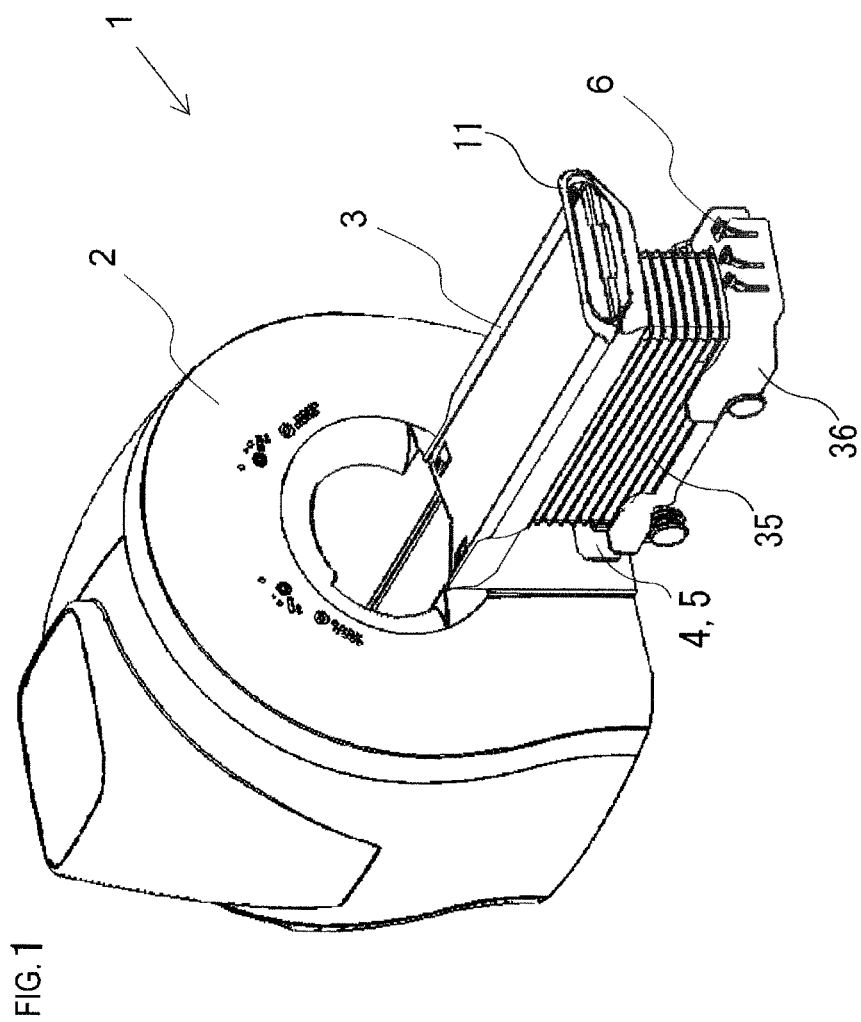
FIG. 1 is a perspective view of a medical imaging apparatus of the present embodiments.

In the invention, a medical imaging apparatus is configured as follows as a first aspect. That is, a medical imaging apparatus of the invention has an apparatus main body equipped with an imaging function of an object, a movable bed, and coupling mechanisms arranged on an apparatus main body side and a bed side, respectively, in order to detachably couple the bed to the apparatus main body. The coupling mechanism on the bed side includes a coupling plate having one end fixed to the bed. The coupling mechanism on the apparatus main body side includes a plurality of rollers that are arranged side by side along the shape of both sides of the coupling plate of the bed when the bed is coupled to the apparatus main body. The coupling plate is sandwiched and held from both the sides by the plurality of rollers during coupling.

It is preferable that two pairs of rollers among the plurality of rollers be arranged at positions where the rollers sandwich the coupling plate. Additionally, it is preferable that the other plurality of rollers be guide rollers that lead the coupling plate between the two pairs of rollers.

The coupling plate has, for example, a substantially trapezoidal shape in which the width of an end portion on the apparatus main body side is smaller than the width of an end portion on the bed side and both sides are linear. In this case, it is preferable to fix the two pairs of rollers at positions where the rollers sandwich both the linear sides.

It is possible to arrange a hook on the coupling plate. In this case, the coupling mechanism on the apparatus main body side is configured so as to include a coupling bar to be engaged with the hook. It is preferable that the bed be equipped with an operating unit that operates the hook, and with the coupling mechanism that couples the operating unit and the hook.

Additionally, according to a second aspect of the invention, a medical imaging apparatus as follows is provided. That is, a medical imaging apparatus of the invention has an apparatus main body equipped with an imaging function of an object, a movable bed, and coupling mechanisms arranged on an apparatus main body side and a bed side, respectively, in order to detachably couple the bed to the apparatus main body. The coupling mechanism either on the apparatus main body side or on the bedside includes a coupling plate. The other coupling mechanism includes a holding member that, during coupling, respectively contacts both side surfaces of the coupling plate at two or more points, and sandwiches and holds the coupling plate from both sides.

It is preferable to adopt a configuration in which the coupling plate is included in the coupling mechanism on the bed side, and the holding member is included in the coupling mechanism on the apparatus main body side.

It is possible to adopt a configuration in which the holding member include two pairs of protrusions, and the two pairs of protrusions be fixed to positions where the protrusions sandwich the coupling plate on both side surfaces. For example, two pairs of rollers can be used as the two pairs of protrusions.

It is possible to adopt a configuration in which the coupling plate is fixed so as to protrude toward the apparatus main body along a long-axis direction of the bed.

It is preferable that both the sides of the coupling plate be linear. In this case, the holding member is configured to respectively contact and hold both side surfaces of the linear coupling plate at two or more points.

As a coupling plate, for example, there is used a coupling plate having a substantially trapezoidal shape in which the width of an end portion on the apparatus main body side is smaller than the width of an end portion on the bed side.

It is also possible to have a structure in which the coupling plate is coupled to the coupling mechanism on a holding member side by a hook.

It is also possible to adopt a configuration in which the coupling mechanism including the holding member has a guide member that guides the coupling plate so as to be led between the guide member and the holding member. In this case, rollers, a guide wall, pins, or the like can be used as the guide member.

Hereinafter, embodiments of the invention will be specifically described with reference to the drawings.

A medical imaging apparatus 1, as shown in FIG. 1, includes an apparatus main body 2 and a bed 3. The apparatus main body 2 may have any configuration as long as an image of a subject mounted on the bed 3 may be captured. For example, a main body of an MRI apparatus or a CT apparatus can be used. Here, a case where the medical imaging apparatus 1 is the MRI apparatus will be described below as an example.

The apparatus main body 2 is configured to include a gantry equipped with a static magnetic field generator that generates a static magnetic field, a gradient magnetic field coil, a radio frequency (RF) magnetic field pulse transmitting coil, and a shim plate, and a gantry cover that covers the gantry. In the example of FIG. 1, the static magnetic field generator of the gantry is in the shape of a cylinder in which an axial direction is made horizontal, and the internal space of the cylinder serves as an imaging space. However, the invention is not limited to the cylindrical static magnetic field generator.

Moreover, the MRI apparatus includes a gradient magnetic field power amplifier that supplies an electric current to the gradient magnetic field coil, a radio frequency power amplifier that supplies a radio frequency signal to the RF magnetic field pulse transmitting coil, a radio frequency amplifying circuit, a computer, an operating unit, and a display, as a power source, control, and signal processing system.

The apparatus main body 2 is arranged in an electromagnetically shielded room, and the power source, control, and signal processing system is arranged outside the electromagnetically shielded room and is electrically connected to the apparatus main body with a cable.

The static magnetic field generator generates a static magnetic field in the imaging space, and the shim plate generates a magnetic field that improves the uniformity of the static magnetic field to a predetermined value or higher. The gradient magnetic field coil generates gradient magnetic fields in predetermined XYZ directions, respectively, in the imaging space. The RF magnetic field pulse transmitting coil transmits an RF magnetic field pulse to the imaging space.

The computer outputs control signals to the gradient magnetic field power amplifier, the radio frequency power amplifier, and the radio frequency amplifying circuit, and controls the application timing and direction of a gradient magnetic field, the irradiation timing of an RF magnetic field pulse, or the like according to a predetermined imaging sequence. Accordingly, the nuclear magnetic-resonance (NMR) signal produced from an object is received by a receiving coil arranged near the object. The radio frequency amplifying circuit detects and amplifies this signal under the control of the computer, and the computer reconstructs an image according to a predetermined image reconstruction program, and displays the image on a display or the like. The operating unit receives imaging conditions or the like from an examiner.

Figure 2:
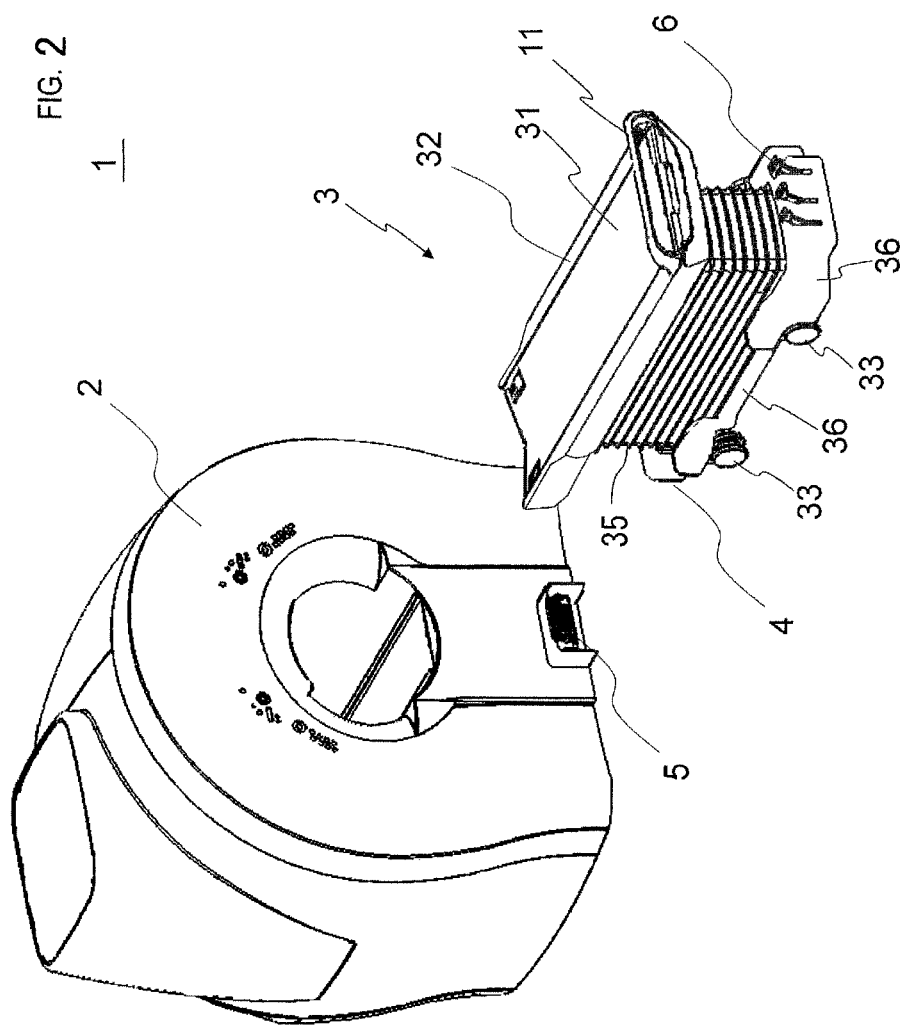
FIG. 2 is a perspective view of the state of the medical merging apparatus of FIG. 1 where a bed 3 is separated from an apparatus main body 2.

As shown in FIG. 2, the bed 3 includes a top plate 31 that allows an object to be mounted thereon, a top plate holding portion 32 that holds the top plate 31, a frame that holds the top plate holding portion 32 so as to be vertically movable, and a vertical drive unit that vertically moves the top plate holding portion 32, a horizontal drive mechanism that horizontally moves the top plate 31 with respect to the top plate holding portion 32, a horizontal drive unit that drives the horizontal drive mechanism, four wheels 33 that are attached to a lower portion of the frame, and bellows portions 35 and a cover 36 that cover an outer periphery of the frame, and a handle portion 11. By virtue of these configurations, the bed 3 can be inserted into an imaging region by raising the top plate 31 to the height of the imaging space of the gantry of the apparatus main body 2 and making the top plate 31 slide horizontally with respect to the top plate holding portion 32. This allows an imaging site of an object to be transported to the center of the imaging space.

In the invention, the bed 3 is attachable to and detachable from the apparatus main body 2. An object can be mounted on the bed by pushing the handle portion 11 of the bed 3 separated from the apparatus main body 2 as shown in FIG. 2 with his/her hands and moving the bed to a lobby, a hospital room of the object, or the like where the magnetism of the apparatus main body 2 does not reach. After the mounting, the bed can be docked with the apparatus main body 2 as shown in FIG. 1 in a state where the object is mounted.

A front end portion of the bed 3 and a front surface of the apparatus main body 2 are respectively equipped with docking units 4 and 5 as the coupling mechanisms. As the docking units 4 and 5 are fitted to each other, the bed 3 is coupled to the apparatus main body 2. Additionally, one or more pedals 6 are installed at a rear end portion of the bed 3.

First Embodiment

The docking units 4 and 5 of a first embodiment will be specifically described.

Figure 3:
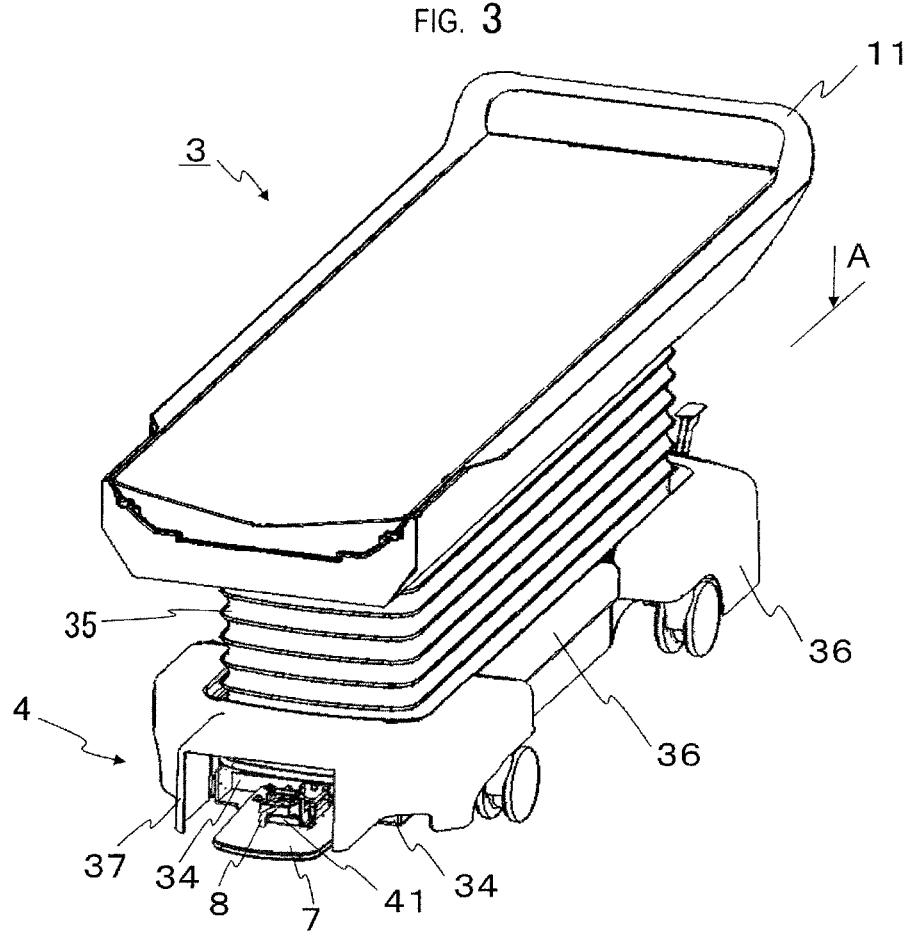
FIG. 3 is a perspective view of the bed 3 of FIG. 1.
Figure 4:
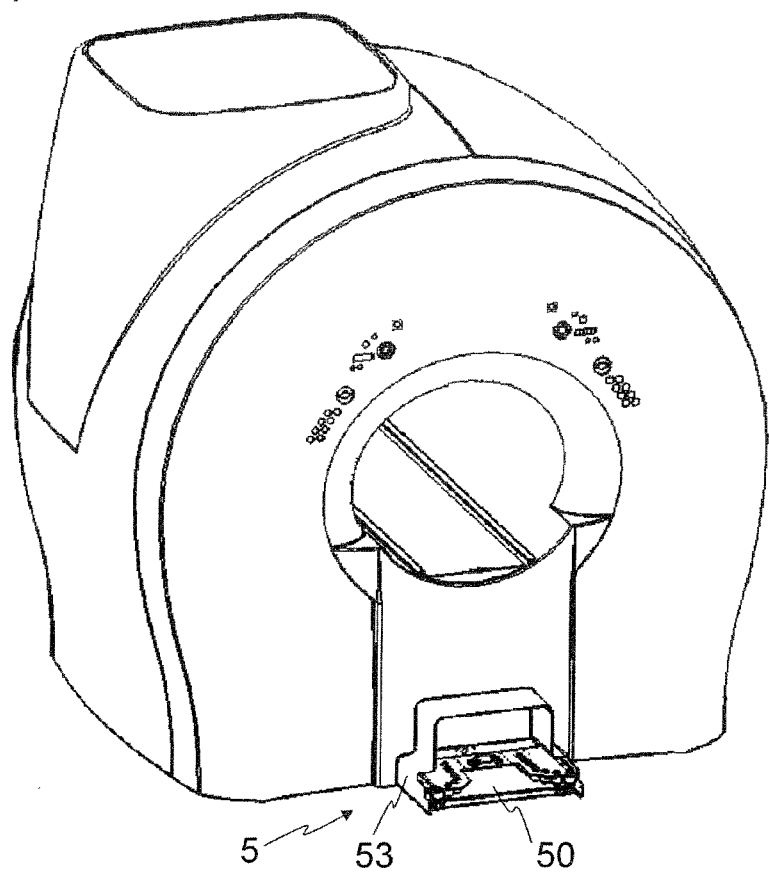
FIG. 4 is a perspective view of the apparatus main body 2 of FIG. 1.
Figure 5:
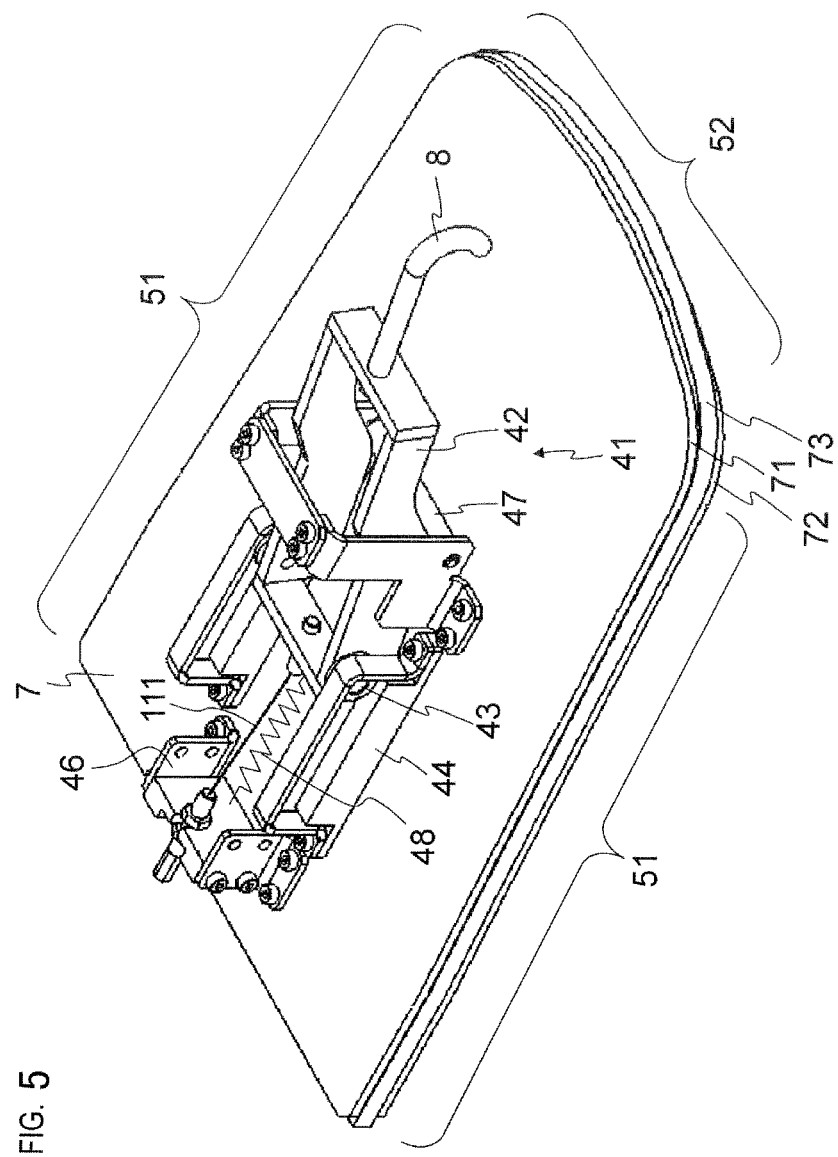
FIG. 5 is a perspective view of a coupling plate 7 of a docking unit 4 on a bed 3 side of a first embodiment.
Figure 6:
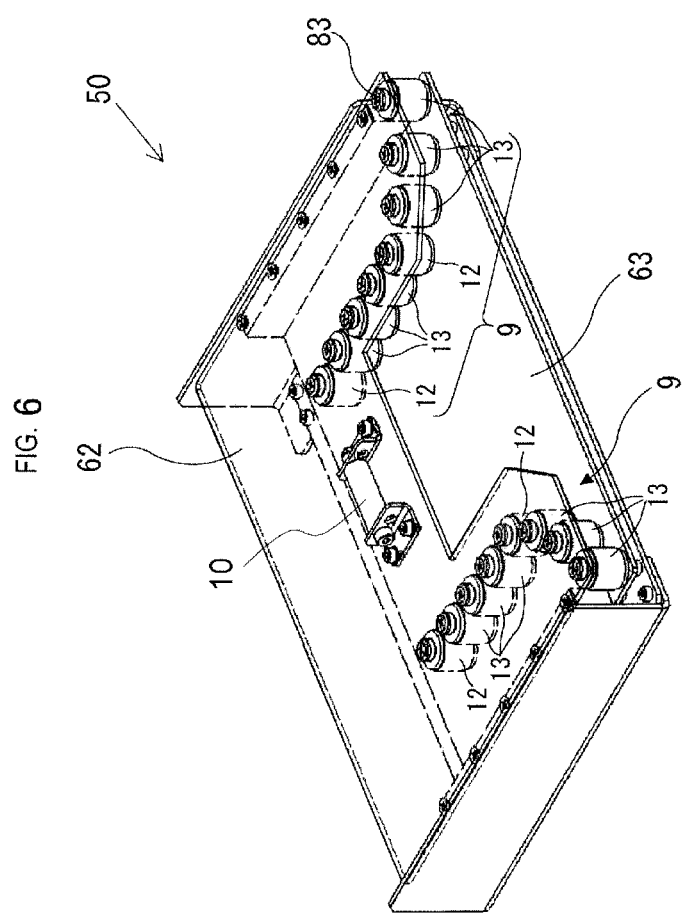
FIG. 6 is a perspective view of a roller unit 50 on an apparatus main body 2 side of the first embodiment.

A perspective view of the bed 3 is shown in FIG. 3, and a perspective view of the apparatus main body 2 is shown in FIG. 4. FIG. 5 is a perspective view of a coupling plate 7 of the docking unit 4 on a bed 3 side. FIG. 6 is a perspective view of a roller unit 50 of the docking unit 5 on an apparatus main body 2 side.

As shown in FIGS. 3 to 5, the docking unit 4 on the bed 3 side includes the coupling plate 7 having one end fixed to a frame 34 of the bed 3, a hook 8, a drive mechanism 41 of the hook 8, and a cover 37. Meanwhile, as shown in FIGS. 4 and 6, the docking unit 5 on the apparatus main body 2 side includes the roller unit 50 in which a plurality of rollers 9 are arranged, a coupling bar 10 for coupling with the hook B, and a cover 53. Members that constitute the docking units 4 and 5 are all nonmagnetic members.

The coupling plate 7 of the bed 3 is inserted into the roller unit 50 of the apparatus main body 2, and the bed 3 is fixed in a lateral direction (the width direction of the bed 3) as the coupling plate 7 is sandwiched from side surface directions between the plurality of rollers 9. Additionally, provided is a structure in which the bed 3 is fixed in the long-axis direction thereof as the hook 8 is coupled to the coupling bar 10. At this time, the cover 37 and the cover 53 are configured so that one cover enters the other cover and there is no collision.

As shown in FIG. 5, the outer shape of the coupling plate 7 is substantially trapezoidal, and has the straight portions 51 on both sides and the curved portion 52 at a tip. In the invention, by forming both the sides in a linear shape (straight portions 51), the coupling plate 7 can be strongly sandwiched and held by the rollers 9 from both the sides. The coupling plate 7 has a shape such that rubber 73 is sandwiched between an upper plate 71 and a lower plate 72, both of which are substantially trapezoidal and made of a non-magnetic metal. The rubber 73 does not protrude further outward than the upper plate 71 and the lower plate 72 in the portions of the straight portions 51 on both the sides, and protrudes slightly from the upper plate 71 and the lower plate 72 only in the curved portion 52 at the tip.

As the metallic upper plate 71 and lower plate 72 form the side surfaces of the coupling plate 7 at the straight portions in this way, the coupling plate 7 is held with a strong force by the rollers 9. Additionally, as the rubber 73 protrudes slightly in the curved portion 52 at the tip, the noise generated when the coupling plate 7 collides against the rollers 9 is reduced. The relationship between the outer shape of the coupling plate and a holding force will be described in detail below.

The drive mechanism 41 of the hook 8 is fixed at a predetermined position on the coupling plate 7. The drive mechanism 41 of the hook 8 includes a hook supporting portion 42 that is fixed to a base of the hook 8, protrusions 43 that are respectively fixed to both the sides of the hook supporting portion 42, slide guides 44 that slidably guide the protrusions 43 along the long-axis direction of the bed 3, a wire A 111 that is fixed to a rear end of the hook supporting portion 42, a wire guide 46, and a bar 47 on which the hook supporting portion 42 rides and that lifts the tip of the hook 8. The other end of the wire A 111 is coupled to the pedal 6 at a rear end of the bed 3. Additionally, a spring 48 is arranged between the rear end of the hook supporting portion 42 and the wire guide 46 to bias the hook supporting portion 42 in a direction in which the hook supporting portion is advanced to the front. In addition, although FIG. 5 is a perspective view, the spring 48 is drawn in a simplified manner for convenience of illustration. The spring 48 may be a spring having any structure.

Figure 7:
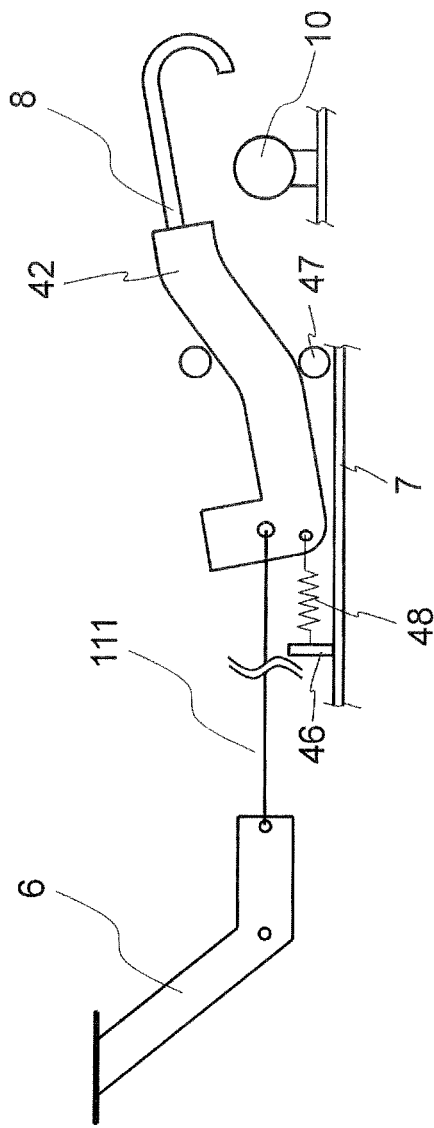
FIG. 7 is a view illustrating the operation of a hook of the docking unit 4 on the bed 3 side of the first embodiment.

FIG. 7 shows the posture of the hook supporting portion 42, a pulling direction of the wire A 111, and a biasing direction of the spring 48. The hook supporting portion 42 is pushed out forward (in a direction of the hook 8) by the force of the spring 48 in a state where the wire A 111 is not pulled, that is, in the state of FIG. 5, a lower surface of the hook supporting portion 42 rides on the bar 47, and the tip of the hook 8 is lifted. If the wire A 111 is pulled backward (in a direction of the pedal 6) through the operation of the pedal 6 by an examiner, the lower surface of the hook supporting portion 42 moves backward along the slide guides 44 while sliding on the upper surface of the bar 47. The lower surface of the hook supporting portion 42 is curved upward at a tip portion thereof. Therefore, as the tip curved upward as it moves backward comes to the position of the bar 47, the hook 8 at the tip moves backward while descending. Accordingly, the hook supporting portion is configured so as to be coupled to the coupling bar 10 on the apparatus main body 2 side. If the wire A 111 is loosened through the operation of the pedal 6, the spring 48 biases the hook supporting portion 42 in a direction in which the hook supporting portion is advanced to the front, the hook supporting portion 42 rides on the bar 47, and the hook 8 is lifted upward and separated from the coupling bar 10.

Meanwhile, as shown in FIG. 6, the roller unit 50 on the apparatus main body 2 side includes an upper plate 62, a lower plate 63, and the plurality of rollers 9 that are arranged between the upper plate 62 and the lower plate 63 and are rotatably fixed. The coupling plate 7 of the bed 3 is inserted into a space between the upper plate 62 and the lower plate 63, and side surfaces thereof are held by the rollers 9. The coupling bar 10 is fixed to a predetermined position on the upper plate 62. The portion of the upper plate 62 closer to the near side than the coupling bar 10 is cut out. Accordingly, when the coupling plate 7 is inserted into the roller unit 50, the hook 8, and its drive mechanism 41 on the coupling plate 7 approach the coupling bar 10 without colliding against the upper plate 62, and are arranged at positions where coupling is allowed.

Figure 8:
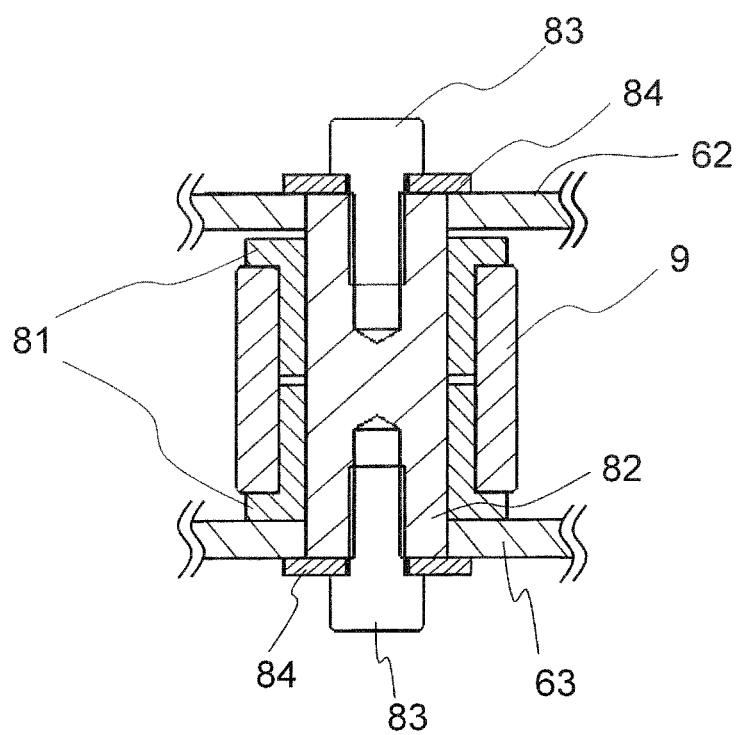
FIG. 8 is a cross-sectional view of a roller 9 of the roller unit 50 of FIG. 6.

A cross-sectional view of a roller 9 is shown in FIG. 8. A shaft 82 of the roller 9 has both ends firmly fixed to the upper plate 62 and the lower plate 63 by screws 83 and washers 84. A sliding bearing 81 is arranged at an outer periphery of the shaft 82, and the roller 9 is arranged at an outer periphery of the sliding bearing 81. The roller 9 and the sliding bearing 81 are integrated and rotates around the shaft 82. The shaft 82 and the roller 9 are made of metal with high rigidity, and the sliding bearing 81 is also made of materials having high rigidity and excellent slidability. Accordingly, even if the coupling plate 7 is inserted into the roller unit 50 and advances while contacting the roller 9, the rollers 9 can sandwich and hold the inserted coupling plate 7 between the rollers 9 without being deformed and warped.

The plurality of arrayed rollers 9 of the roller unit 50, as shown in FIG. 6, are constituted by four (two pairs of) supporting rollers 12 and a plurality of guide rollers 13. At a final docking position, the supporting rollers 12 contact the coupling plate 7 and sandwiches and fixes the coupling plate 7 from both the sides. When the coupling plate 7 is inserted into the roller unit 50, the guide rollers 13 function to guide the movement of the coupling plate 7 and lead the coupling plate to the docking position.

Figure 9:
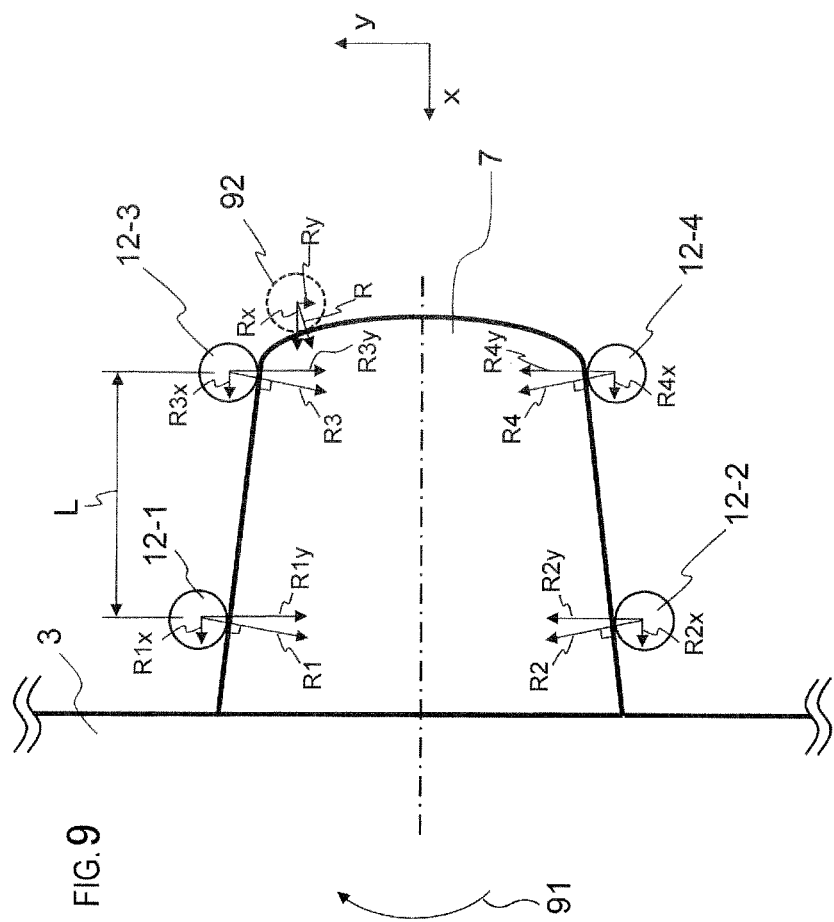
FIG. 9 is a view showing the positional relationship and roller reaction forces between supporting rollers 12 of the roller unit 50 and the coupling plate 7 of FIG. 6.

FIG. 9 is an explanatory view showing the positional relationship between the four (two pairs of) supporting rollers 12 and the coupling plates 7 at the docking position. The four supporting rollers 12-1 to 12-4, as shown in FIG. 9, are arranged so as to sandwich the straight portions 51 of the coupling plate 7 from both the sides. Specifically, a pair of the supporting roller 12-1 and the supporting roller 12-2 are arranged face to face at the positions of the coupling plate 7 near the frame 34, and, a pair of the supporting roller 12-3 and the supporting roller 12-4 are arranged face to face at positions near at the tip of the coupling plate 7. The spacing between the supporting rollers 12-1 and 12-2 and the spacing between the supporting rollers 12-3 and 12-4, as shown in FIG. 9, are set to exactly the same widths as the widths of the positions of the coupling plate 7 at the docking position. That is, since the coupling plate 7 is substantially trapezoidal, the spacing between the supporting rollers 12-1 and 12-2 is wider than the spacing between the supporting rollers 12-3 and 12-4. Accordingly, the coupling plate 7 is sandwiched by the four supporting rollers 12 and does not advance forward any more, at the docking position of FIG. 9, and is positioned by the four supporting rollers 12 at the docking position.

Additionally, it is preferable that the spacing L between the supporting roller 12-1 or 12-2 and the supporting roller 12-3 or 12-4 be longer because the coupling plate 7 can be held with a large holding force even in a case where the bed 3 sways left and right or a turning force works around the coupling plate 7.

Figure 10:
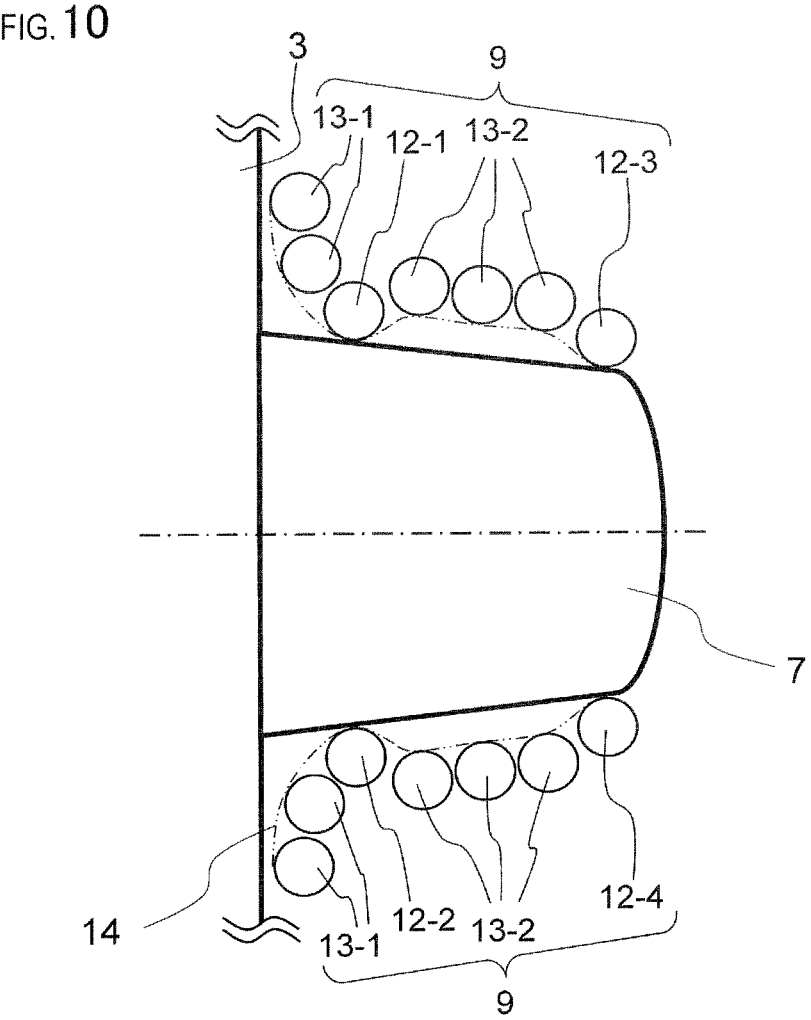
FIG. 10 is a top view showing the arrangement of the rollers 9 of the roller unit of FIG. 6.

FIG. 10 is an explanatory view showing the positional relationship between the guide rollers 13 and the coupling plate 7 at the docking position. As shown in FIG. 10, the guide rollers 13-1 located further toward the bed 3 side than the supporting rollers 12-1 and 12-2 are arranged in a curved line 14 so as to constitute a frontage leading the coupling plate 7 between the supporting rollers 12-1 and 12-2, on an entrance side of the roller unit 50.

That is, the spacing between the guide rollers 13-1 is wider than the spacing between the supporting roller 12-1 and the supporting roller 12-2 in a short-axis direction of the bed 3. Accordingly, the positional deviation of the bed 3 with respect to the apparatus main body 2 can be corrected, and the bed can be led to the docking position. The guide rollers 13-2 located between the supporting rollers 12-1 and 12-2 and the supporting rollers 12-3 and 12-4 are arranged so as to correct the orientation of the tips of the coupling plate 7 inserted between the supporting rollers 12-1 and 12-2 and lead the coupling plate between the supporting rollers 12-3 and 12-4. In addition, the guide rollers 13-1 and 13-2 are arranged so as to be offset to positions farther from the coupling plate 7 than the supporting rollers 12 so that, during docking, the four supporting rollers 12 reliably contact and hold the side surfaces of the coupling plate 7 and the guide rollers 13-1 and 13-2 do not contact the coupling plate 7.

Figure 11:
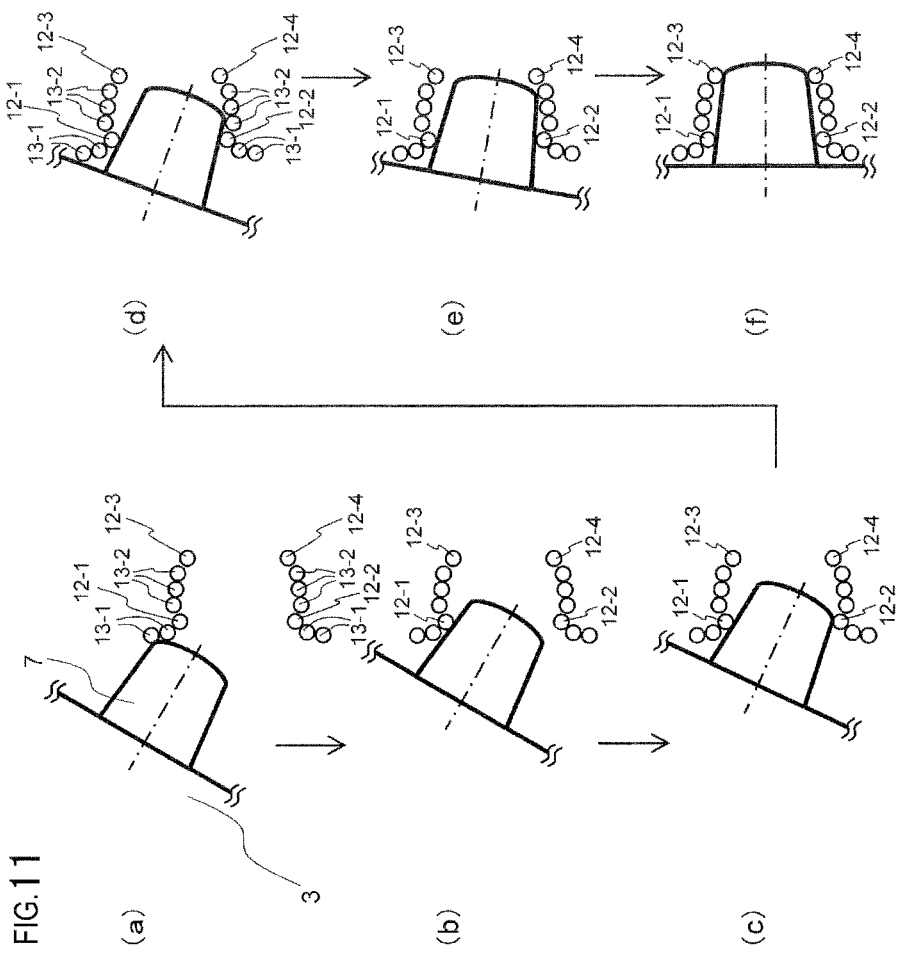
FIGS. 11(a) to 11(f) are views showing the operation of inserting the coupling plate 7 into the roller unit of FIG.

The movement of the coupling plate 7 when the bed 3 is docked with the apparatus main body 2 will be described with reference to FIG. 11. An examiner holds the handle portion 11 of the bed 3 to move the bed 3 toward the apparatus main body 2 during docking. Since the supporting rollers 12 and the guide rollers 13 are arranged at the roller unit 50 as described above, if the bed 3 approaches the apparatus main body, the coupling plate 7 of the bed 3 contacts the guide roller 13-1 of the roller unit 50 of the apparatus main body 2, and the deviations of the position and the angle of the bed 3 with respect to the apparatus main body 2 are corrected (FIGS. 11(a) and 11(b)). Accordingly, the tip of the coupling plate 7 is inserted between the supporting rollers 12-1 and 12-2 (FIG. 11(c)).

If the examiner further advances the bed 3, the tip of the coupling plate 7 contacts the guide roller 13-2, and thereby, the deviation of the position and the angle is corrected (FIGS. 11(d) and 11(e)), and the coupling plate is led between the supporting rollers 12-3 and 12-4 on the tip end side (FIG. 11(f)). Since the coupling plate 7 cannot be inserted anymore if the coupling plate is inserted to a position where the spacing between the supporting rollers 12-1 and 12-2, and the spacing between the supporting rollers 12-3 and 12-4 coincide with the widths of the coupling plate 7 at the positions of the supporting rollers, the movement of the bed 3 stops. This position is a docking position.

Figure 12:
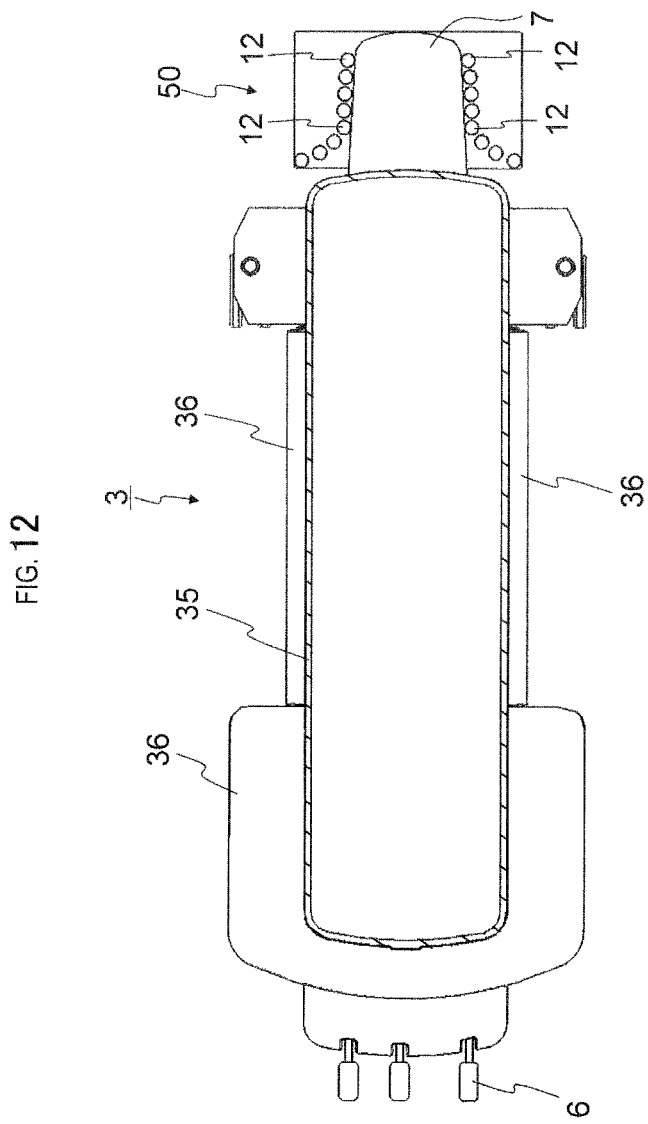
FIG. 12 is a cross-sectional view of the bed 3 and the roller unit 50 in a coupled state, in the first embodiment.

FIG. 12 is a view showing the positional relationship among the bed 3, the coupling plate 7, and the roller unit 50 at the docking position. FIG. 12, which is a cross-sectional view of the bed at position A of FIG. 3, shows only the coupling plate 7 in a state where the cover 41 is removed from the docking unit 4, and omits the other configuration. In the apparatus main body 2, only the supporting rollers 12 and guide rollers 13 of the docking unit 5 are shown. As shown in FIG. 12, it can be seen that the bed 3 is held at the roller unit 50 of the apparatus main body 2 by the coupling plate 7 narrower than the bellows portion 35 in the short-axis direction of the bed 3.

If the bed 3 is inserted into the docking position and the examiner operates the pedal 6 to pull the wire A 111, the hook 8 moves in the direction in which the hook is pulled to the rear side (bed 3 side) while descending, and is coupled to the coupling bar 10 on the apparatus main body 2 side. From the above, the docking operation is completed.

In contrast, when the bed 3 is separated from the apparatus main body 2, the hook 8 is lifted and removed from the coupling bar 10 if the examiner operates the pedal 6 to loosen the wire A 111. If the examiner holds the handle portion 11 and pulls the bed backward, the bed can be separated from the apparatus main body 2.

Here, the relationship between the shape of the coupling plate 7 and the holding force received from the supporting rollers 12 will be described with reference to FIG. 9. If an external force in the horizontal direction is applied to the bed 3 in a docking state, since the coupling plate 7 is pushed against the supporting rollers 12 by the external force, the coupling plate 7 receives roller reaction forces from the pushed supporting rollers 12. Roller reaction forces R1 to R4 are forces directed in directions perpendicular to the side surfaces of the coupling plate 7 from the respective supporting rollers 12-1 to 12-4. Component forces R1y to R4y in the horizontal direction y (the width direction of the bed 3) of the roller reaction forces and the external force are balanced with each other and hold the bed 3. For example, if a force that turns the bed 3 in a direction of arrow 91 of FIG. 9 is applied, the coupling plate 7 receives the roller reaction forces R1 and R4 from the supporting roller 12-1 and the supporting roller 12-4, and component forces R1y and R4y thereof in the horizontal direction are balanced with the external force, and the coupling plate is held. That is, the force of turning the bed 3 can be cancelled by the moment of the supporting rollers 12 arranged in the long-axis direction of the bed 3.

Additionally, since the straight portions 51 incline, component forces R1x to R4x in a bed long-axis direction x of the roller reaction forces R1 to R4 are generated. The component forces R1x to R4x are forces in a direction in which the coupling plate 4 is pushed out from the apparatus main body 2. In the configuration of the present embodiment, the tension of the wire A 111 of the hook 8 is balanced with the component forces R1x to R4x, and thereby pushing-out of the coupling plate 4 is suppressed. The tension of the wire A 111 is designed to be greater than the total of R1x to R4x.

Here, if the supporting rollers 12 contact the curved portion 52 of the coupling plate 7 as in a roller 92 shown by a dotted line in FIG. 9, the component forces Ry in the horizontal direction of the roller reaction forces R become small, and the component forces Rx in the bed long-axis direction become large. For this reason, the force of holding the bed 3 in the horizontal direction becomes small, whereas the force of pushing out the bed 3 from the apparatus main body 2 becomes large. Therefore, in the present embodiment, it is desirable to arrange the four rollers 9 so as to contact the straight portions of the coupling plate 7.

Additionally, in the present embodiment, the coupling plate 7 is made substantially trapezoidal and the straight portions 51 are inclined. Therefore, when the bed 3 is attached to and detached from the apparatus main body 2, as shown in FIG. 11, the bed can be inserted into the docking unit 5 of the apparatus main body 2 from an oblique direction or can be separated from the docking unit in an oblique direction.

Accordingly, even if an electromagnetic shielding chamber in which the apparatus main body 2 is arranged is narrow, it is possible to attach and detach the bed 3.

However, the invention is not limited to the substantially trapezoidal coupling plate 7. When the electromagnetic shielding chamber in which the apparatus main body 2 is arranged is sufficiently wide and the bed 3 can be straightly lowered until the coupling plate 7 is separated from the roller unit 50, it is also possible to form the coupling plate 7 into a substantially oblong shape. In this case, since the component forces R1x to R4x in the bed long-axis direction x, of the roller reaction forces R1 to R4 are not generated, all the roller reaction forces can be used so as to be balanced with the external force in the horizontal direction applied to the bed 3, and the holding force can be improved. Additionally, it is possible to make the tension of the wire A 111 small.

Additionally, in the present embodiment, the guide rollers 13 are arranged. However, it is also possible to omit some or all of the plurality of guide rollers 13.

As described above, the configuration of the present embodiment is a configuration in which the external force applied in the horizontal direction of the bed 3 is received by the reaction forces of the two pairs of supporting rollers 12 arranged in the long-axis direction of the bed 3. Therefore, although it is preferable that the length (the long-axis direction of the bed 3) of the coupling plate 7 be longer, it is not necessary to increase the width of the coupling plate 7. For this reason, although the configuration of the present embodiment is a configuration in which the bed 3 and the apparatus main body 2 can be coupled by a sufficient holding force during docking, the bed can be sufficiently held even if the width (the short-axis direction of the bed 3) of the coupling plate 7 is narrow. In the example of FIG. 12, the width (the short-axis direction of the bed 3) of the coupling plate is narrower than the width (the short-axis direction of the bed 3) of the bellows portion 35. In this way, a narrow docking mechanism that does not hinder the examiner's access to an object can be provided.

In the present embodiment, the coupling plate 7 is arranged on the bed 3 side and the roller unit 50 is arranged on the apparatus main body 2 side. However, it is also possible to arrange the roller unit 50 on the bed 3 side and to arrange the coupling plate 7 on the apparatus main body 2 side. It should be noted that it is more preferable to arrange the coupling plate 7 on the bed 3 side as in the first embodiment in the viewpoint of ensuring a wider space under the examiner's feet at a lower portion of the bed 3 because the width of the roller unit 50 becomes greater than the width of the coupling plate 7 structurally.

Additionally, by installing the guide rollers 13 in addition to the supporting rollers 12, the allowable width of the positional deviation of the bed 3 with respect to the apparatus main body 2 is large, and the examiner's work of docking the bed 3 with the apparatus main body 2 can be easily performed.

Additionally, by arranging the guide rollers 13 in a curved line, the coupling plate 7 can be smoothly inserted into the roller unit 50.

Additionally, the present embodiment is configured so that the rubber 73 is sandwiched between the upper side plate 71 and the lower side plate 72 of the coupling plate 7 and the rubber 73 protrudes only in the curved portion 52. However, it is also possible to form the side surfaces of the coupling plate 7 only from a metal plate without arranging the rubber 73.

Second Embodiment

Figure 13:
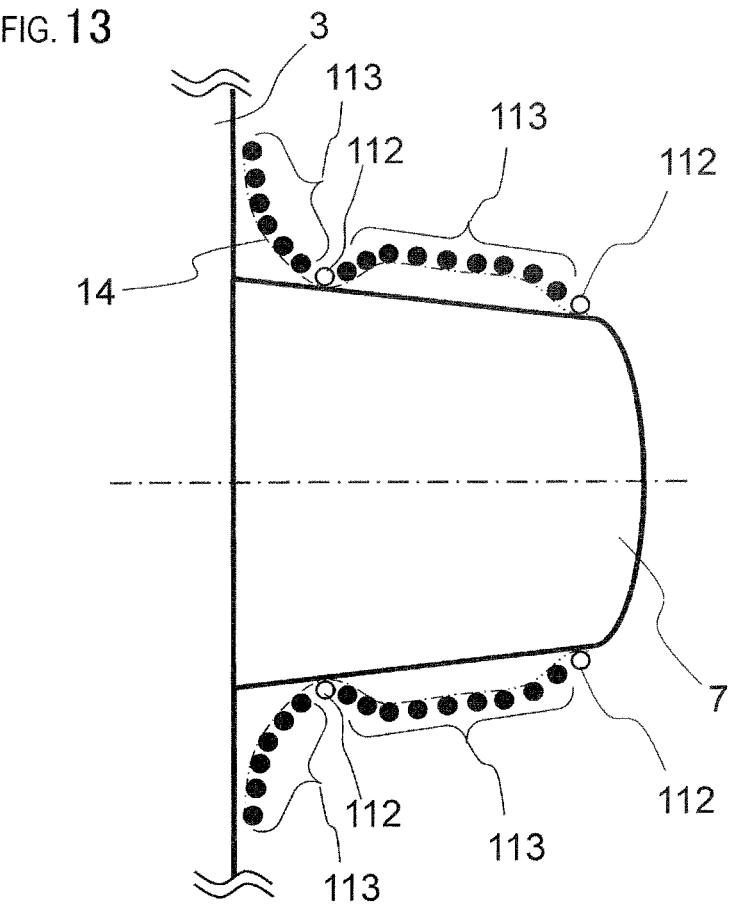
FIG. 13 is a view showing a coupling plate 7 of a second embodiment and the positions of supporting pins 1120 and guide pins 1130 holding the coupling plate.

A roller unit 50 of a second embodiment will be described with reference to FIG. 13. In the second embodiment, two pairs of supporting pins 1120 and guide pins 1130 that are not rollers (do not rotate) are used instead of the supporting rollers 12 and the guide rollers 13 of the first embodiment. The positions of the supporting pins 1120 and the guide pins 1130 are the same as the positions of the supporting rollers 12 and the guide rollers 13, respectively. The other structure is made to be the same as that of the first embodiment.

Accordingly, almost the same functions as in the roller unit 50 of the first embodiment can be obtained.

Additionally, the number of parts can be reduced because the shafts and bearings of the supporting rollers 12 and the guide rollers 13 become unnecessary by using the supporting pins 1120 and guide pins 1130 instead of the supporting rollers 12 and the guide rollers 13.

Third Embodiment

Figure 14:
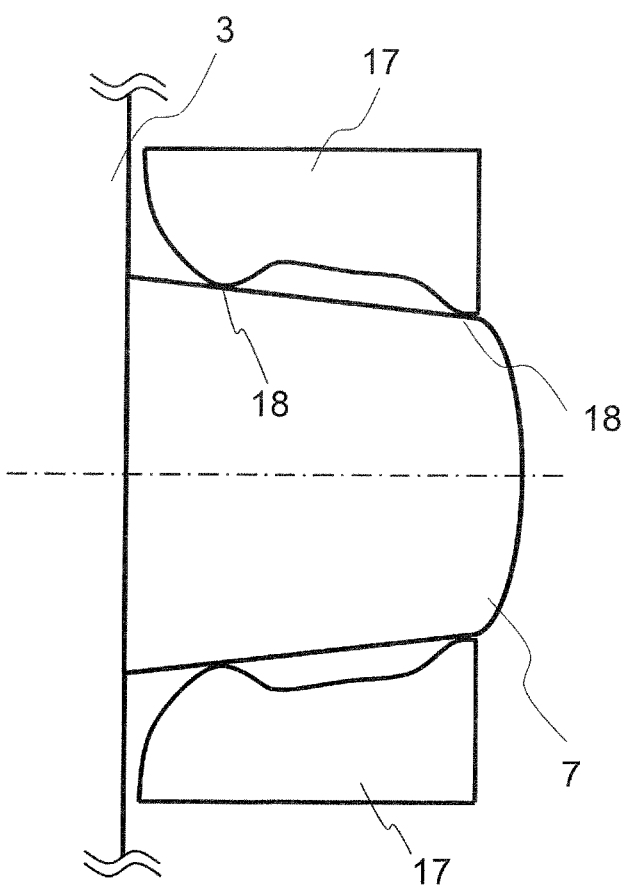
FIG. 14 is a view showing a coupling plate 7 of a third embodiment, and the shape of a guide wall 17 holding the coupling plate.

A roller unit 50 of a third embodiment will be described with reference to FIG. 14. A guide wall 17 in the same shape as the curved line 14 of FIG. 10 is installed instead of the supporting rollers 12 and the guide roller 13 of the first embodiment. The guide wall 17 has supporting points 18 at the same positions as the four supporting rollers 12 of the first embodiment. During docking, the guide wall 17 contacts the coupling plate 7 at the our (two pairs) supporting points (protrusions) 18 and holds the coupling plate 7. The other portions of the guide wall 17 guide the insertion of the coupling plate 7, similar to the guide rollers 13 of the first embodiment. The other structure is made to be the same as that of the first embodiment.

Accordingly, almost all of the same functions as in the roller unit 50 of the first embodiment can be obtained. Additionally, the number of parts can be reduced because the shafts and bearings of the supporting rollers 12 and the guide rollers 13 become unnecessary by using the guide wall 17 instead of the supporting rollers 12 and the guide rollers 13.

It is desirable to select the material of the guide wall 17 so that friction does not become excessively large during contact with the material of the coupling plate 3. For example, one or both of the guide wall 17 and the coupling plate 7 are made of materials having excellent slidability.

Additionally, as shown in FIG. 15, the coefficient of friction with the guide wall 17 can also be made low by installing coupling plate rollers 19 at an outer periphery of the coupling plate 7.

REFERENCE SIGNS LIST

1: MEDICAL IMAGING APPARATUS
2: APPARATUS MAIN BODY
3: BED
4: DOCKING UNIT
5: DOCKING UNIT
6: PEDAL
7: COUPLING PLATE
8: HOOK
9: ROLLER
10: COUPLING BAR
12: SUPPORTING ROLLER
13: GUIDE ROLLER
14: CURVED LINE
1120: SUPPORTING PIN
1130: GUIDE PIN
17: GUIDE WALL
18: SUPPORTING POINT
19: COUPLING PLATE ROLLER
31: TOP PLATE
32: TOP PLATE HOLDING PORTION
33: WHEEL
34: FRAME
35: BELLOWS PORTION
36: COVER
37: COVER
42: HOOK SUPPORTING PORTION
43: PROTRUSION
44: SLIDE GUIDE
46: WIRE GUIDE
47: BAR
45: SPRING
50: ROLLER UNIT
50: STRAIGHT PORTION
52: CURVED PORTION
53: COVER
62: UPPER SIDE PLATE
63: LOWER SIDE PLATE
71: UPPER SIDE PLATE
72: LOWER SIDE PLATE
73: RUBBER
81: SLIDING BEARING
82: SHAFT
83: SCREW
84: WASHER
111: WIRE A

The invention claimed is:

1. A medical imaging apparatus comprising:
an apparatus main body equipped with an imaging function of an object;
a movable bed; and
a coupling mechanism arranged on an apparatus main body side and a coupling mechanism arranged on a bed side, to detachably couple the bed to the apparatus main body,
wherein the coupling mechanism on the bed side includes a coupling plate which has a substantially trapezoidal shape in which the width of an end portion on the apparatus main body side is smaller than the width of an end portion on the bed side, and the coupling mechanism on the apparatus main body side includes a holding member that, during coupling, contacts each of two opposing side surfaces of the coupling plate at two or more points, and sandwiches and holds the coupling plate from both sides.

2. The medical imaging apparatus according to claim 1, wherein the apparatus main body is a magnetic resonance imaging apparatus.

3. The medical imaging apparatus according to claim 1, wherein the holding member include two pairs of protrusions, and the two pairs of protrusions are fixed to positions where the protrusions respectively sandwich the coupling plate from both side surfaces.

4. The medical imaging apparatus according to claim 3, wherein the two pairs of protrusions are two pairs of rollers or two pairs of pins.

5. The medical imaging apparatus according to claim 1, wherein the coupling plate is fixed so as to protrude toward the apparatus main body along a long-axis direction of the bed.

6. The medical imaging apparatus according to claim 1, wherein both of the sides of the coupling plate are linear-shaped, and the holding member contacts and holds both side surfaces of the coupling plate at two or more points.

7. The medical imaging apparatus according to claim 1, further comprising:
a mechanism that couples the coupling plate to the coupling mechanism on a holding member side by a hook.

8. The medical imaging apparatus according to claim 1, wherein the coupling mechanism including the holding member has a guide member that guides the coupling plate so as to be led into the holding member.

9. The medical imaging apparatus according to claim 8, wherein the guide member is a pin.

10. The medical imaging apparatus according to claim 8, wherein the guide member is a roller.

11. The medical imaging apparatus according to claim 8, wherein the guide member is a guide wall.

12. A bed for a medical imaging apparatus that is attachable to and detachable from the medical imaging apparatus, and is movable, the bed comprising:
a coupling mechanism that is coupled to the medical imaging apparatus,
wherein the coupling mechanism includes a coupling plate having one end fixed and the other end protruding toward the medical imaging apparatus, and the coupling plate has a substantially trapezoidal shape in which the width of an end portion on an apparatus main body side is smaller than the width of an end portion on a bed side and both sides are linear.

13. The bed for a medical imaging apparatus according to claim 12, wherein a hook is arranged on the coupling plate, an operating unit is provided to operate the hook, and a coupling mechanism is provided to couple the operating unit and the hook.

14. A medical imaging apparatus comprising:
an apparatus main body equipped with an imaging function of an object;
a movable bed; and
a coupling mechanism arranged on an apparatus main body side and a coupling mechanism arranged on a bed side, to detachably couple the bed to the apparatus main body,
wherein the coupling mechanism on the apparatus main body side includes a coupling plate which has a substantially trapezoidal shape in which the width of an end portion on the apparatus main body side is wider than the width of an end portion on the bed side, and the coupling mechanism on the bed side includes a holding member that, during coupling, contacts each of two opposing side surfaces of the coupling plate at two or more points, and sandwiches and holds the coupling plate from both sides.

* * * * *